United States Patent [19]
Dudley et al.

[11] Patent Number: 5,776,721
[45] Date of Patent: Jul. 7, 1998

[54] IN VITRO MODEL FOR STUDY OF THE PHARMACODYNAMICS OF INTRACELLULAR KILLING OF BACTERIA AND VIRUSES

[75] Inventors: Michael N. Dudley; Sean F. Donnelly, both of North Kingston, R.I.; Andrew Strayer, Olathe, Kans.

[73] Assignee: The Board of Governors for Higher Education, State of Rhode Island and Providence Plantations, Providence, R.I.

[21] Appl. No.: 512,458

[22] Filed: Aug. 8, 1995

[51] Int. Cl.⁶ .............. C12Q 1/02; C12Q 1/04; C12Q 1/00; C12N 7/00
[52] U.S. Cl. .............. 435/29; 435/34; 435/4; 435/5; 435/7.32; 435/235.1; 435/240.2; 435/240.21; 435/240.22; 435/240.23; 435/253.1; 435/863; 436/63; 436/74
[58] Field of Search .............. 435/29, 34, 4, 435/7.32, 235.1, 240.2, 240.21, 240.22, 240.23, 253.1, 258.3, 256.7, 863; 436/63, 74

[56] References Cited

U.S. PATENT DOCUMENTS

| | | | |
|---|---|---|---|
| 4,783,484 | 11/1988 | Violante et al. | 435/29 |
| 5,215,914 | 6/1993 | Lo et al. | 435/7.32 |
| 5,350,673 | 9/1994 | Campbell et al. | 435/29 |
| 5,364,763 | 11/1994 | Kacian | 435/7.32 |
| 5,447,861 | 9/1995 | Collins et al. | 435/240.21 |
| 5,494,660 | 2/1996 | Hunter et al. | 435/29 |
| 5,534,413 | 7/1996 | Lo et al. | 435/7.32 |

*Primary Examiner*—Louise Leary
*Attorney, Agent, or Firm*—Samuels, Gauthier, Stevens & Reppert

[57] ABSTRACT

Adherent cell lines are grown on cover slips. The cover slips are placed in a culture media containing fluctuating concentrations of drugs for the purpose of testing simulated drug dosage regimens for use in the treatment of human infection. The cover slips are removed and the cells are harvested and processed for viable bacterial numbers of viral DNA over time.

3 Claims, 2 Drawing Sheets

IN VITRO MODEL FOR STUDY OF THE PHARMACODYNAMICS OF INTRACELLULAR KILLING OF BACTERIA AND VIRUSES

BACKGROUND AND BRIEF SUMMARY OF THE INVENTION

The usual methods for determining antibiotic activity, either alone or in combination, generally expose a growing bacterial inoculum to a constant or static concentration of one or more drugs for a fixed period. Such methods include disk susceptibility tests, determinations of minimal inhibitory and minimal bactericidal concentrations with microtiter or macrotube dilutions and time-kill studies. Even the determination of serum bactericidal activity in patients or volunteers receiving a given antibiotic regimen only ascertains the antibiotic activity at a specific time, at a single concentration of drug or drugs.

However, during the clinical treatment of an infection in patients, bacteria growing at an infected site are exposed to a continuously changing concentration of antibiotics and when two drugs of differing elimination half-lives are administered, the ratios of the concentrations of these drugs also change.

Several in vitro models that incorporate pharmacokinetic parameters in the in vitro test system have been developed. Many of these models stimulate serum, tissue or urine concentrations achieved following the intravenous, intramuscular or oral administration of an antibiotic and some can be used to study two drugs in combination.

In this disclosure the term pharmacodynamic in vitro model will be used to refer to in vitro systems which expose bacteria to changing antibiotic concentrations that mimic human pharmacokinetics.

In vitro models allow for comparisons of antibacterial efficacy of newly developed antibiotics with the efficacy of older drugs. In contrast to conventional in vitro method such comparisons consider pharmacokinetic differences of the drugs tested. Also the simulation of multiple dosing regimens allows for the study of emerging resistance under conditions which are closer to the in vivo situation than during conventional static in vitro testing.

In addition to their use for the preclinical study of antibiotics, pharmacodynamic models are also suitable for the study of optimal dosing and scheduling of antibiotics.

Various designs of in vitro models have been used to expose bacterial cultures to continuously changing antibiotic concentrations. In such in vitro models bacterial cultures containing virus-infected cells are exposed to drug concentrations which change over time according to the concentrations profiles achieved during clinical treatment in serum, interstitial fluid, tissue or urine. Bacterial counts and/or turbidimetric measurements and/or quantification of viral particles are determined periodically to assess the antibacterial effects.

There are several known pharmacodynamics techniques used.

One-compartment models expose a bacterial culture to continuously changing concentrations of an antibiotic. In this model a dose of an antibiotic is injected into the culture flask as soon as the bacterial inoculum reaches the required density. The drug culture is then continuously diluted by pumping sterile antibiotic-free culture medium into the compartment at a fixed pump rate, resulting in a linear dilution of both bacteria and antibiotic.

For most antibiotics the serum kinetics following intravenous administration is described by a monoexponential decrease over the period of a dosing interval, reflecting the rate at which the antibiotic is eliminated from the body.

A problem with one-compartment in vivo models includes dilution of the test organism in the process of diluting the drug at the desired elimination rate. This has been overcome by a two-compartment system. Commercially available capillary units have been used to construct a two-compartment model that exposes bacteria to concentrations of one or two antibiotics mimicking human pharmacokinetics in interstitial fluid following intravenous, oral, or intramuscular administration. Briefly, extravascular infection sites are represented in this model by artificial capillary units which contain bacterial cultures within the peripheral compartments. The units consist of a plastic tube through which runs a bundle of hollow fibers of cellulose or polysulfone. The hollow fibers in the bundle have porous walls acting as a membrane. The peripheral compartments interface with the central compartment through the porous capillary walls which allow for bidirectional penetration of antibiotics but prevent the passage of large molecules or bacterial cells. Bacteria are placed through a sampling port into the outer chamber of the artificial capillary units, the so-called peripheral chambers. Several capillary units are placed in series and are connected with plastic tubing to a central reservoir. The content of the central reservoir plus the lumen of the capillaries and the tubing connecting the units represent the central reservoir.

In practice, antibiotic is administered into the central reservoir. The antibiotic-containing broth of the central compartment is continuously pumped through the capillaries. The antibiotic penetrates through the permeable walls of the capillaries into the peripheral chambers containing the bacteria. Sterile antibiotic-free broth is continuously pumped into the central compartment at a flow rate set to simulate the elimination half-life of the antibiotic in human subjects. An elimination flask is provided to allow simultaneous removal of antibiotic-containing medium from the central compartment. Thus, the volume in the central compartment stays constant, but the concentration of antibiotic therein is reduced exponentially. It is this changing concentration of antibiotic that is pumped through the capillary units to achieve changing antibiotic levels within the peripheral chambers, which contain the bacteria, see e.g. Blaser et al., In vitro models for the study of antibiotic activities, Progress in Drug Research, 1987, 315, 349–81.

The successful application of the pharmacodynamic models reported in the literature to date has been directed to the study of non-adherent bacterial cultures. The use of these models for adherent cell lines or intracellular bacteria has not been widely practiced because the bacteria does not remain uniformly suspended in a liquid medium. It is believed the most relevant art is Vergeres et al., Amikacin, Ceftazidime, and Flucloxacillin against Suspended and Adherent *Pseudomonas aeruginosa* and *Staphlococcus epidennidis* in an In Vitro Model of Infection, J.I.D 1992: 165 (February). This reference teaches coating glass beads with a bacterial biofilm, placing the coated beads in a culture into which is introduced an antibiotic and removing the beads at various times to assay the killing of bacterium adhered to the surfaces of the beads.

The invention broadly relates to a method and device which overcomes the problem of dosage regimen design in the drug therapy of infections due to intracellular bacteria.

The invention, in one aspect, embodies growing adherent mammalian cell lines infected with intracellular bacterial pathogens, such as *Mycobacterium sp.* and *Legionelia sp.*, or viruses such as herpes viruses, on the surface of removable supports, (such as microscope cover slips). These supports are placed in a culture medium containing fluctuating concentrations of drugs for the purposes of testing simulated drug dosage regimens for use in the treatment of human infection. The supports are removed and the cells are harvested and processed for viable bacterial numbers or viral DNA over time. The invention embodies, in another aspect, the study of drug treatment of bacteria or pathogens found in the intracellular space of certain cells, such as macrophages, neutrophils and lymphocytes using conventional in vitro models.

The invention in still another aspect embodies a module designed to function with an in vitro model to study the pharmacodynamics of drugs in infected or uninfected adherent cell lines. The module supports an array of cover slips suspended and submerged in medium by way of a series of springs held within a frame. The module holds the cover slips securely with minimal surface contact to avoid disturbance of the cells on the surface. The module allows even circulation of the medium across the surfaces of the cover slips as well as great accessibility to and ease of extraction of the cover slips from the chamber at various time intervals.

In a preferred embodiment, the module comprises a perimeter support and longitudinal members secured to the perimeter support in substantially parallel relationship. Each of the longitudinal members is characterized by a plurality of walls and adjacent walls define slots. The slots of one longitudinal member are essentially in register with, or aligned with, the slots of the next side-by-side longitudinal member such that the insertion and removal of cover slips into and out of a pair of adjacent slots is facilitated. In a particularly preferred embodiment, the longitudinal members comprise extension springs with the adjacent coils of each spring defining the slots. The coils are biased toward one another. In this manner when the cover slips are secured between adjacent coils they are securely held in frictional engagement between the adjacent coils or walls.

In the process of the invention the bacteria or virus infected cell lines are grown on the cover slips in a vessel containing medium as described for a one-compartment pharmaco-dynamic model. The growing culture is exposed to changing concentrations of a drug(s). The cover slips, at the desired time, are removed from the vessel and the cells are processed and the bacteria or amount of virus quantified. The module of the invention can be used in any or all of the three described steps.

DESCRIPTION OF THE PREFERRED EMBODIMENT(S)

Figure 1:
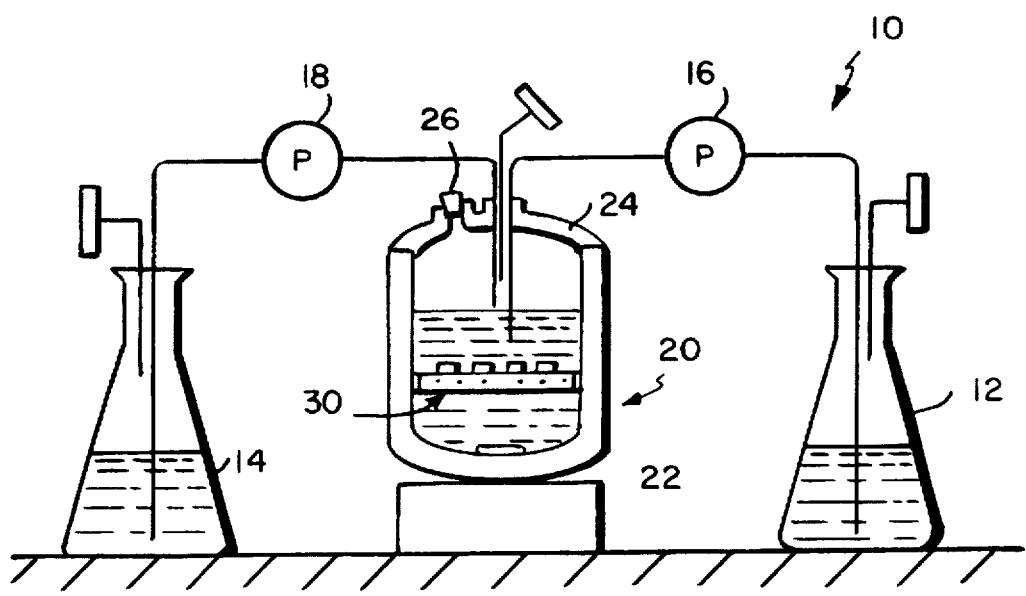
FIG. 1 is an illustration of a one-compartment pharmacokinetic model.

Referring to FIG. 1, an in-vitro cover slip suspension module embodying the invention in a prior art one-compartment model is shown generally at 10 and comprises a diluent reservoir 12, an eliminating reservoir 14 together with associated pumps 16 and 18 respectively. A culture compartment 20 is supported on a stirrer 22. The culture compartment 20 further includes a cover 24 characterized by a sample access port 26. A module embodying the invention is shown at 30.

Figure 3:
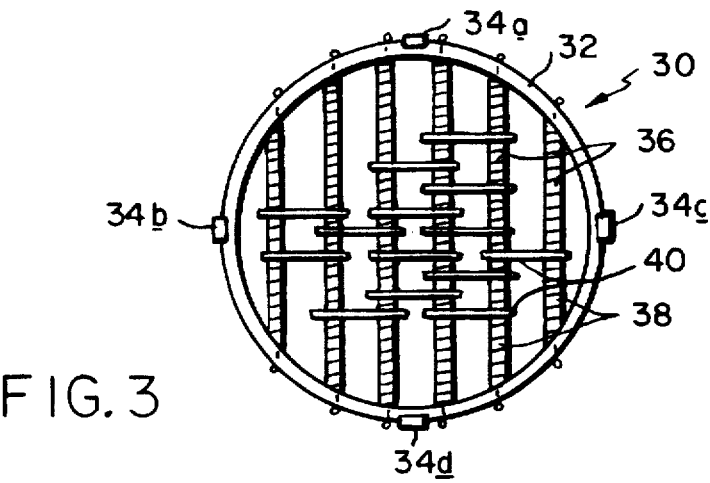
FIG. 3 is a plan view of a component of FIG. 2.
Figure 2:
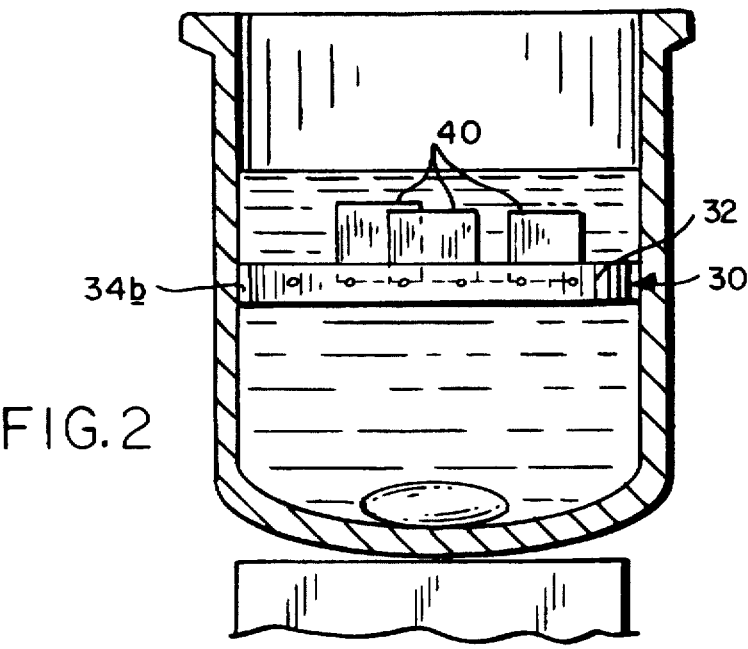
FIG. 2 is a front sectional view of a module embodying the invention.
Figure 4:
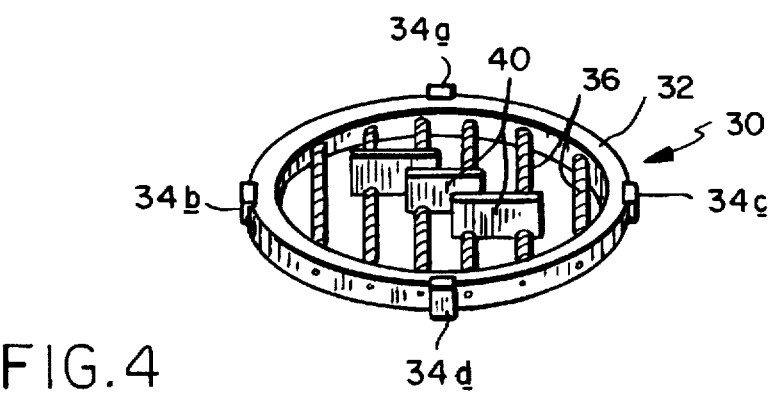
FIG. 4 is a perspective view of the module supporting cover slips.

The module 30 is shown more clearly in FIGS. 2, 3 and 4. Referring to FIG. 2, the module 30 is shown received in the culture compartment 20 and comprises a ring-like member 32. The member 32 frictionally engage the sides of the culture compartment 20 to ensure stability. Secured in the outer wall of the member 30 are bushings 34a, 34b, 34c and 34d spaced 90° apart. The bushings ensure the member 32 will remain in place while cover slips are inserted into and removed from the member 30. Alternatively adhesive-like pads or a continuous adhesive-like strip may be secured on the outer wall surface.

Referring to FIG. 3, the member 32 is shown in greater detail and has secured thereto in parallel relationship extension springs 36 with adjacent coils 38 defining slots therebetween.

Referring to FIG. 4, cover slips 40 on the surfaces of which has been grown adherent cell lines are received between opposed coils 38 of the springs 36. The spring being an extension spring results in an inherent bias of the coils of the spring toward one another. Thus, when the cover slips are inserted between adjacent coils, the coils deflect slightly outward and secure the cover slip therebetween. As shown in the drawings, the slots defined by the coils of the adjacent extension springs are substantially aligned one to the other to facilitate the insertion of the cover slips into slots defined by the coils.

The module supports, in a releasable manner, cover slips suspended and submerged in media in a culture compartment. The slips are readily accessible and are easily removed for analysis at specific moments in time. The module is autoclavable and lends itself to maintaining sterility, allows the media to circulate freely through the bioreactor and evenly circulate around the cover slips. The module holds a maximum number of cover slips, has the least possible surface contact with the cover slips while holding the cover slips firmly in place. Although extension springs are preferred because of the inherent elasticity between adjacent coils, other structures can achieve the same result. For example, a flat strip having wells formed therein to receive the lower portion of the cover slips could be used. The walls of the wells would engage the cover slips to prevent inadvertent dislodgement. The walls and bottom of the wells should be apertures or perforated.

The perimeter of the module which holds the springs is essentially determined by the configuration of the inner surface of the bioreactor. That is, to maximize the number of cover slips that can be received in the bioreactor, the perimeter of the frame holding the springs substantially corresponds to the inner surface of the bioreactor. The frame sits against the inner surface and is suspended or spaced apart from the bottom of the bioreactor to allow a magnetic stir-bar to be used to enhance the circulation of the media. This open design allows even circulation and flow of the media across the surface of the slips. Support legs can be secured to the frame if desired.

The module is used in a preferred embodiment where cell lines infected with a pathogen are adhered to cover slips and exposed to oscillating drug concentrations mimicking human serum kinetics during clinical treatment. The method allows superior assessment of the drugs affect against the pathogen because the cover slips can be easily removed from a media at predetermined times and the affect of the drug arrayed. The cover slips, as will be described, are removed at various sampling times during the test period.

With the invention, the adherent cell lines (e.g. macrophages) infected with bacteria (or uninfected to study cellular pharmacology) on the surfaces of cover slips are immersed in a culture medium. A drug is introduced into the reservoir and removed over time by controlled dilution with drug free medium. The dilution rate is controlled by a pump system adjusted to mimic the drug elimination half-life observed in humans. The cover slips are removed at varying times and processed to determine the number of bacteria surviving drug exposure, assayed for the concentration of drug or other product of cells, such as antigens, cytokines or proteins.

In the operation of the invention, adherent cell lines, e.g. mouse macrophages, are grown on standard plastic microscope cover slips. The cells are infected with a pathogen, e.g. mycrobacterium avium-complex. The growth of the adherent cell lines and their infection with a pathogen is well known in the art and need not be described in detail.

The module 30, as shown in FIG. 1, is placed in a medium, such as RPMI 1640., and the cover slips are inserted between adjacent coils 38 of the extension springs as shown in FIG. 3. The stirrer 22 is actuated and the drug being tested, e.g. ciprofloxacin, is introduced into the media. Drug-free media from the reservoir 12 flows into the media at a rate of 2 ml/min. The medium is withdrawn from the bioreactor and into the eliminating reservoir 14 at the same rate as the culture is added.

At predetermined time intervals, e.g. every 24 hours, the cover slips are removed and assayed to determine the drugs effectiveness. For the preferred embodiment, the assay comprises lysing the cells and quantifying the bacteria.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for the in vitro assay of intracellular pathogenic infected adherent cell lines which comprises:

providing cover slips having at least one surface;

adhering the cell lines on the surfaces of the cover slips in substantially uniform quantities on each of said surfaces;

placing the cover slips in a common culture media in a culture compartment;

introducing a drug into the culture media;

varying the concentration of the drug in the media;

removing at least one of the cover slips from the media at time $T_1$ when the drug is at a first concentration; assaying the cells removed at time $T_1$;

removing another of the cover slips at time $T_2$ when the drug is at a second concentration; and assaying the cells removed at time $T_2$ from the cover slips for intracellular pathogens.

2. The method of claim 1 wherein the pathogens infecting the adherent cell lines are intracellular bacterial pathogens.

3. The method of claim 2 wherein the pathogens are bacterial pathogens selected from the group consisting of *Mycobacterium sp.*, *Legionella sp.*, or *Chlamydia sp.*, or viruses.

\* \* \* \* \*

UNITED STATES PATENT AND TRADEMARK OFFICE
CERTIFICATE OF CORRECTION

PATENT NO. : 5,776,721
DATED : July 7, 1998
INVENTOR(S) : Michael N. Dudley, Andrew Strayer It is certified that error appears in the above-identified patent and that said Letters Patent is hereby corrected as shown below:

On the title page, change Item [75] to read as follows:

Inventors: Michael N. Dudley, North Kingston, R.I.; Andrew Strayer, Olathe, Kans.

Signed and Sealed this

Fifth Day of January, 1999

Attest:

Attesting Officer

*Acting Commissioner of Patents and Trademarks*